(12) United States Patent
Simon et al.

(10) Patent No.: US 8,634,897 B2
(45) Date of Patent: *Jan. 21, 2014

(54) TRAJECTORY STORAGE APPARATUS AND METHOD FOR SURGICAL NAVIGATION SYSTEMS

(75) Inventors: David A. Simon, Boulder, CO (US);
Kevin T. Foley, Memphis, TN (US);
Thomas A. Carls, Memphis, TN (US);
Anthony J. Melkent, Lafayette, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 209 days.

This patent is subject to a terminal disclaimer.

(21) Appl. No.: 12/966,407

(22) Filed: Dec. 13, 2010

(65) Prior Publication Data

US 2011/0077508 A1 Mar. 31, 2011

Related U.S. Application Data

(63) Continuation of application No. 11/128,808, filed on May 13, 2005, now Pat. No. 7,853,305, which is a continuation of application No. 10/177,739, filed on Jun. 21, 2002, now Pat. No. 6,920,347, which is a continuation of application No. 09/545,092, filed on Apr. 7, 2000, now Pat. No. 6,535,756.

(51) Int. Cl.
*A61B 5/055* (2006.01)

(52) U.S. Cl.
USPC .......................................... 600/424; 600/407

(58) Field of Classification Search
USPC ................................. 600/407, 424
See application file for complete search history.

(56) References Cited

U.S. PATENT DOCUMENTS

| | | | |
|---|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |

(Continued)

FOREIGN PATENT DOCUMENTS

| | | |
|---|---|---|
| CA | 964149 | 3/1975 |
| DE | 3042343 A1 | 6/1982 |

(Continued)

OTHER PUBLICATIONS

European Search Report completed Jul. 7, 2011 for European Patent Application No. EP10183461 filed Sep. 30, 2010; which claims benefit of EP019231729, filed Sep. 21, 2002; which claims benefit of PCT/US2001/011116, filed Apr. 6, 2001; which claims benefit of U.S. Appl. No. 09/545,092, filed Apr. 7, 2000.

(Continued)

*Primary Examiner* — Peter Luong
(74) *Attorney, Agent, or Firm* — Harness, Dickey (57) ABSTRACT

A method and apparatus for determining, calculating, and/or viewing a trajectory. The trajectory can be displayed on a display relative to image data of a patient. A user can use the system to determine relationships between two or more trajectories that have been determined. The relationships can be within two dimensional, three-dimensional, or four dimensional space. The relationships can include distance, angle, etc. The relationships can also be determined between real time trajectories and stored trajectories, or combinations thereof.

26 Claims, 5 Drawing Sheets

(56) References Cited

U.S. PATENT DOCUMENTS

| | | |
|---|---|---|
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,259,725 A | 3/1981 | Andrews et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |

(56) References Cited

U.S. PATENT DOCUMENTS

| | | |
|---|---|---|
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,221,283 A | 6/1993 | Chang |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,345,938 A | 9/1994 | Nishiki et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,369,678 A | 11/1994 | Chiu et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,403,321 A | 4/1995 | DiMarco |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |

(56) References Cited

U.S. PATENT DOCUMENTS

| | | |
|---|---|---|
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,752,962 A | 5/1998 | D'Urso |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,833,627 A | 11/1998 | Shmulewitz et al. |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,900 A | 9/1999 | Derbyshire et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,957,844 A | 9/1999 | Dekel et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |

(56) References Cited

U.S. PATENT DOCUMENTS

| | | |
|---|---|---|
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,021,342 A | 2/2000 | Brabrand |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,194,639 B1 | 2/2001 | Botella et al. |
| 6,201,387 B1 | 3/2001 | Govari |
| 6,203,497 B1 | 3/2001 | Dekel et al. |
| 6,211,666 B1 | 4/2001 | Acker |
| 6,223,067 B1 | 4/2001 | Vilsmeier et al. |
| 6,233,476 B1 | 5/2001 | Strommer et al. |
| 6,246,231 B1 | 6/2001 | Ashe |
| 6,246,898 B1 | 6/2001 | Vesely et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,381,485 B1 | 4/2002 | Hunter et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,535,756 B1 | 3/2003 | Simon et al. |
| 6,551,325 B2 | 4/2003 | Neubauer et al. |
| 6,584,174 B2 | 6/2003 | Schubert et al. |
| 6,609,022 B2 | 8/2003 | Vilsmeier et al. |
| 6,611,700 B1 | 8/2003 | Vilsmeier et al. |
| 6,640,128 B2 | 10/2003 | Vilsmeier et al. |
| 6,694,162 B2 | 2/2004 | Hartlep |
| 6,701,179 B1 | 3/2004 | Martinelli et al. |
| 6,920,347 B2 | 7/2005 | Simon et al. |
| 7,853,305 B2 | 12/2010 | Simon et al. |
| 2001/0007918 A1 | 7/2001 | Vilsmeier et al. |
| 2002/0095081 A1 | 7/2002 | Vilsmeier et al. |
| 2004/0024309 A1 | 2/2004 | Ferre et al. |

FOREIGN PATENT DOCUMENTS

| | | |
|---|---|---|
| DE | 3508730 | 9/1986 |
| DE | 3717871 | 12/1988 |
| DE | 3831278 A1 | 3/1989 |
| DE | 3838011 | 7/1989 |
| DE | 4213426 A1 | 10/1992 |
| DE | 4225112 | 12/1993 |
| DE | 4233978 C1 | 4/1994 |
| DE | 19715202 | 10/1998 |
| DE | 19751761 | 10/1998 |
| DE | 19832296 | 2/1999 |
| DE | 19747427 | 5/1999 |
| DE | 10085137 | 11/2002 |
| EP | 0062941 | 10/1982 |
| EP | 0119660 | 9/1984 |
| EP | 0155857 | 9/1985 |
| EP | 0319844 | 6/1989 |
| EP | 0326768 | 8/1989 |
| EP | 350996 A1 | 1/1990 |
| EP | 0359773 A1 | 3/1990 |
| EP | 0419729 A1 | 4/1991 |
| EP | 0427358 | 5/1991 |
| EP | 0456103 | 11/1991 |
| EP | 0469966 A1 | 2/1992 |
| EP | 0501993 A1 | 9/1992 |
| EP | 0581704 | 2/1994 |
| EP | 0651968 | 5/1995 |
| EP | 0655138 | 5/1995 |
| EP | 0894473 A2 | 2/1999 |
| EP | 0908146 | 4/1999 |
| EP | 0930046 | 7/1999 |
| FR | 2417970 | 9/1979 |
| FR | 2618211 A1 | 1/1989 |
| GB | 2094590 A | 9/1982 |
| GB | 2164856 A | 4/1986 |
| JP | 62327 | 1/1983 |
| JP | 2765738 | 6/1988 |
| JP | 63240851 | 10/1988 |
| JP | 3267054 | 11/1991 |
| JP | 6194639 | 7/1994 |
| WO | WO-8809151 | 12/1988 |
| WO | WO-8905123 | 6/1989 |
| WO | WO-9005494 A1 | 5/1990 |
| WO | WO-9103982 A1 | 4/1991 |
| WO | WO-9104711 | 4/1991 |
| WO | WO-9107726 | 5/1991 |
| WO | WO-9203090 | 3/1992 |
| WO | WO-9206645 | 4/1992 |
| WO | WO-9404938 | 3/1994 |
| WO | WO-9423647 | 10/1994 |
| WO | WO-9424933 A1 | 11/1994 |
| WO | WO-9507055 A1 | 3/1995 |
| WO | WO-9611624 | 4/1996 |
| WO | WO-9632059 A1 | 10/1996 |
| WO | WO-9703609 | 2/1997 |
| WO | WO-9731581 A1 | 9/1997 |
| WO | WO-9736192 A1 | 10/1997 |
| WO | WO-9740764 A2 | 11/1997 |
| WO | WO-9749453 A1 | 12/1997 |
| WO | WO-9808554 A1 | 3/1998 |
| WO | WO-9838908 | 9/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |

(56) References Cited

FOREIGN PATENT DOCUMENTS

| WO | WO-9952094 A1 | 10/1999 |
|---|---|---|
| WO | WO-9960939 A1 | 12/1999 |
| WO | WO-0130437 A1 | 5/2001 |

OTHER PUBLICATIONS

Adams et al., Computer-Assisted Surgery, IEEE Computer Graphics & Applications, pp. 43-51, (May 1990).
Adams, L., et al., "Aide au Reperage Tridimensionnel pour la Chirurgie de la Base du Crane," Innov. Tech. Biol. Med., vol. 13, No. 4, pp. 409-424 (1992).
Barrick et al., "Prophylactic Intramedullary Fixation of the Tibia for Stress Fracture in a Professional Athlete," Journal of Orthopaedic Trauma, vol. 6, No. 2, pp. 241-244 (1992).
Barrick et al., "Technical Difficulties with the Brooker-Wills Nail in Acute Fractures of the Femur," Journal of Orthopaedic Trauma, vol. 6, No. 2, pp. 144-150 (1990).
Barrick, "Distal Locking Screw Insertion Using a Cannulated Drill Bit: Technical Note," Journal of Orthopaedic Trauma, vol. 7, No. 3, 1993, pp. 248-251.
Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.
Benzel, E., et al. "Magnetic Source Imaging: A Review of the Magnes System of Biomagnetic Technologies Incorporated," Neurosurgery, vol. 33, No. 2 (Aug. 1993).
Bergstrom et al. Stereotaxic Computed Tomography, Am. J. Roentgenol, vol. 127 pp. 167-170 (1976).
Bouazza-Marouf, K., et al., "Robotic assisted internal fixation of femoral fractures," Journal of Engineering in Medicine, Proc. Instn. Mech. Engrs., vol. 209, pp. 51-58 (1995).
Brack et al., "Accurate X-ray Based Navigation in Computer-Assisted Orthopedic Surgery," CAR '98, pp. 716-722.
Brown, R., M.D., A Stereotactic Head Frame for Use with CT Body Scanners, Investigative Radiology .COPYRGT. J.B. Lippincott Company, pp. 300-304 (Jul.-Aug. 1979).
Brunie, L., et al., Pre-and intra-irradiation multimodal image registration: principles and first experiments, Radiotherapy and Oncology 29, pp. 244-252 (1993).
Bryan, "Bryan Cervical Disc System Single Level Surgical Technique", Spinal Dynamics, 2002, pp. 1-33.
Bucholz, R.D., et al., "A Comparison of Sonic Digitizers Versus Light Emitting Diode-Based Localization," Interactive Image-guided Neurosurgery, Chapter 16, pp. 179-200 (1993).
Bucholz, R.D., et al., "Image-guided surgical techniques for infectious and trauma of the central nervous system," Neurosurg. Clinics of N.A., vol. 7, No. 2, pp. 187-200 (1996).
Bucholz, R.D., et at., "The Correction of Stereotactic Inaccuracy Caused by Brain Shift Using an Intraoperative Ultrasound Device," First Joint Conference, Computer Vision, Virtual Reality and Robotics in Medicine and Medical Robotics and Computer-Assisted Surgery, Grenoble, France, pp. 459-466, (Mar. 19-22, 1997).
Bucholz, R.D., et al., "Variables affecting the accuracy of stereotactic localization using computerized tomography," J. Neurosurg., vol. 79, pp. 667-673 (1993).
Bucholz, R.D., et al., Intraoperative localization using a three dimensional optical digitizer, SPIE-The Intol Soc. For Opt. Eng., vol. 1894, pp. 312-322 (Jan. 17-19, 1993).
Champleboux et al., "Accurate Calibration of Cameras and Range Imaging Sensors: the NPBS Method," IEEE International Conference on Robotics and Automation, Nice, France, May 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," International Advanced Robotics Programme, Sep. 1989, pp. 63-65.
Cinquin, P., et al., "Computer Assisted Medical Interventions," IEEE, pp. 254-263 (May/Jun. 1995).

Clarysse, P., et al., "A Computer-Assisted System for 3-D Frameless Localization in Stereotaxic MRI," IEEE Trans. on Med. Imaging, vol. 10, No. 4, pp. 523-529 (Dec. 1991).
Cutting M.D. et al., Optical Tracking of Bone Fragments During Craniofacial Surgery, Second Annual International Symposium on Medical Robotics and Computer Assisted Surgery, pp. 221-225, (Nov. 1995).
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley, "The StealthStation: Three-Dimensional Image-Interactive Guidance for the Spine Surgeon," Spinal Frontiers, Apr. 1996, pp. 7-9.
Foley, K.T., et al., "Image-guided Intraoperative Spinal Localization," Intraoperative Neuroprotection, Chapter 19, pp. 325-340 (1996).
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, CC., et al., "Intracranial Neurosurgery Guided by Functional Imaging," Surg. Neurol., vol. 42, pp. 523-530 (1994).
Galloway, R.L., et al., "Interactive Image-Guided Neurosurgery," IEEE Trans. on Biomed. Eng., vol. 89, No. 12, pp. 1226-1231 (1992).
Galloway, R.L., Jr. et al, Optical localization for interactive, image-guided neurosurgery, SPIE, vol. 2164, pp. 137-145 (May 1, 1994).
Germano, "Instrumentation, Technique and Technology", Neurosurgery, vol. 37, No. 2, Aug. 1995, pp. 348-350.
Germano, Isabelle M., et al., The NeuroStation System for Image-Guided, Frameless Stereotaxy, Neurosurg., vol. 37, No. 2, pp. 348-350 (Aug. 1995).
Gildenberg et al., "Calculation of Stereotactic Coordinates from the Computed Tomographic Scan," Neurosurgery, vol. 10, No. 5, May 1982, pp. 580-586.
Gomez, C.R., et al., "Transcranial Doppler Ultrasound Following Closed Head Injury: Vasospasm or Vasoparalysis," Surg. Neural., vol. 35, pp. 30-35 (1991).
Gonzalez, "Digital Image Fundamentals," Digital Image processing, Second Edition, 1987, pp. 52-54.
Gottesfeld Brown et al., "Registration of Planar Film Radiographs with Computer Tomography," Proceedings of MMBIA, Jun. 1996, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).
Gueziec et al., "Registration of Computed Tomography Data to a Surgical Robot Using Fluoroscopy: A Feasibility Study," Computer Science/Mathematics, Sep. 27, 1996, 6 pages.
Guthrie, B.L., Graphic-Interactive Cranial Surgery: The Operating Arm System, Handbook of Stereotaxy Using the CRW Apparatus, Chapter 13, pp. 193-211 (1994).
Hamadeh et al, "Kinematic Study of Lumbar Spine Using Functional Radiographies and 3D/2D Registration," TIMC UMR 5525—IMAG (1997).
Hamadeh et al., "Automated 3-Dimensional Computed Tomographic and Fluorscopic Image Registration," Computer Aided Surgery (1998), 3:11-19.
Hamadeh, A., "X-Ray data acquisition in OR-Test Specifications, Operative Room Test Report," Laboratoire TIMC, France, pp. 1-9 (Jun. 5, 1995).
Hamadeh, A., et al., "Toward automatic registration between CT and X-Ray images: cooperation between 3D/2D registration and 2D edge detection," TIMC-IMAG, Faculte de Medecine de Grenoble, France, pp. 39-46 (1995)(Second Annual Intl. Symposium onMedical Robotics and Computer-Assisted Surgery, MRCAS '95, Nov. 4-7, 1995).

(56) References Cited

OTHER PUBLICATIONS

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Hatch, "Reference-Display System for the Integration of CT Scanning and the Operating Microscope," Thesis, Thayer School of Engineering, Oct. 1984, pp. 1-189.
Hatch, J.F., "Reference-Display System for the Integration of CT Scanning and the Operating Microscope," IEEE, vol. 8, pp. 252-254, Proceedings of the Eleventh Annual Northwest Bioengineering Conference (Worchester, Massachusetts)(Mar. 14-15, 1985).
Heilbrun et al., "Preliminary experience with Brown-Roberts-Wells (BRW) computerized tomography stereotaxic guidance system," Journal of Neurosurgery, vol. 59, Aug. 1983, pp. 217-222.
Heilbrun, M.P., "Progressive Technology Applications," Neurosurgery for the Third Millenium, Chapter 15, pp. 191-198 (1992) (J. Whitaker & Sons Ltd., Amer. Assoc. of Neurol. Surgeons, Oct. 1992).
Heilbrun, M.P., Computed Tomography-Guided Stereotactic Systems, Clinical Neurosurgery, Chapter 31, pp. 564-581 (1983).
Heilbrun, M.P., et al., "Stereotactic Localization and Guidance Using a Machine Vision Technique," Stereotact. Funct. Neurosurg. Proceed. of the Mtg. of the Amer. Soc. for Stereot. and Funct. Neurosurg. (Pittsburg, PA) vol. 58, pp. 94-98 (1992).
Henderson, J.M., et al., "An Accurate and Ergonomic Method of Registration for Image-Guided Neurosurgery," Computerized Medical Imaging and Graphics, vol. 18, No. 4, pp. 273-277 (1994).
Hoerenz, "The Operating Microscope I. Optical Principles, Illumination Systems, and Support Systems," Journal of Microsurgery, vol. 1, 1980, pp. 364-369.
Hofstetter, R., et al., "Fluoroscopy Based Surgical Navigation-Concept and Clinical Applications," Computer Assisted Radiology and Surgery, CAR '97, Proceed. of the 11th Intl. Symp. and Exh., Berlin, pp. 956-960 (Jun. 25-28, 1997).
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
International Search Report mailed Jul. 5, 2001 for PCT/US01/11116 claiming benefit of U.S. Appl. No. 09/545,092, filed Apr. 7, 2000.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Kall, B., The Impact of Computer and Imgaging Technology on Stereotactic Surgery, Proceedings of the Meeting of the American Society for Stereotactic and Functional Neurosurgery, pp. 10-22 (1987).
Kato, A., et al., "A frameless, armless navigational system for computer-assisted neurosurgery," J. Neurosurg., vol. 74, pp. 845-849 (May 1991).
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," ACTA Neurochirurgica, vol. 68, 1983, pp. 1-9.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., "Long-Term Experience with Different Types of Localization Systems in Skull-Base Surgery," Ear, Nose & Throat Surgery, Chapter 51, pp. 635-638 (1996).
Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., "Navigation Support for Surgery by Means of Optical Position Detection," Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Image guided operating robot: a clinical application in stereotactic neurosurgery," Proceedings of the 1992 IEEE Intemation Conference on Robotics and Automation, May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.
Lavallee, et al., Computer Assisted Medical Interventions, NATO ASI Series, vol. F 60, 3D Imaging in Medic., pp. 301-314 (1990).
Lavallee, S., et al., "Computer Assisted Interventionist Imaging: The Instance of Stereotactic Brain Surgery," MEDINFO 89, pp. 613-617 (1989).
Lavallee, S., et al., "Computer Assisted Spine Surgery: a Technique for Accurate Transpedicular Screw Fixation," TIMC, Faculte de Medecine de Grenoble (pp. 315-322,), J. of Image Guided Surg., vol. 1, No. 1, pp. 65-73 (1995).
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Leavitt, D.D., et al., Dynamic Field Shaping to Optimize Stereotactic Radiosurgery, I.J. Rad. Onc. Biol. Physc., vol. 21, pp. 1247-1255 (1991).
Leavitt, D.D., et al., Dynamic Field Shaping to Optimize Stereotactic Radiosurgery,I.J. Rad. Onc. Biol. Phys., vol. 21, pp. 1247-1255 (1991).
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

(56) References Cited

OTHER PUBLICATIONS

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrate Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, P., et al., "Computer Assisted Spine Surgery," Clinical Orthop. and Related Research, No. 337, pp. 86-96 (1997).

Ng, W.S. et al., Robotic Surgery—A First-Hand Experience in Transurethral Resection of the Prostate Surgery, IEEE Eng. in Med. And Biology, pp. 120-125 (Mar. 1993).

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Pelizzari, C.A., et al., "Accurate Three-Dimensional Registration of CT, PET, and/or MR Images of the Brain," Journal of Computer Assisted Tomography, vol. 13, No. 1, pp. 20-26 (Jan./Feb. 1989).

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F., et al., "Sonic Stereometry in Microsurgical Procedures for Deep-Seated Brain Tumors and Vascular Malformations," Neurosurgery, vol. 32, No. 1, pp. 51-57 (Jan. 1993).

Reinhardt, H.F., et al., Mikrochirugische Entfernung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).

Reinhardt, Hans F., "Neuronavigation: A Ten-year Review," Neurosurgery, pp. 329-341 (1996).

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS 1995, pp. 185-192.

Smith et al., "Computer Methods for Improved Diagnostic Image Display Applied to Stereotactic Neurosurgery," Automedical, vol. 14, 1992, pp. 371-382 (4 unnumbered pages).

Smith, K.R., et al., "Multimodality Image Analysis and Display Methods for Improved Tumor Localization in Stereotactic Neurosurgery," Annual Intl. Conf. of the IEEE Eng. In Med. and Biol. Soc., vol. 13, No. 1, p. 210 (1991).

Smith, K.R., et al., "The Neurostation.TM.—A Highly, Accurate, Minimally Invasive Solution to Frameless Stereotactic Neurosurgery," Comput. Med. Imag. and Graph., vol. 18, No. 4, pp. 247-256 (1994).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Translation (from a French document) by Brian Fish, "Part C—Methodology for Computer Assisted Introduction of a Screw into a Pedicle," Feb. 12, 2001.

Trobraugh, J.W., et al., Frameless Stereotactic Ultrasonography: Method and Applications, Computerized Medical Imaging and Graphics, vol. 18, No. 4, pp. 235-246 (1994).

Troccaz, J., et al., "Conformal External Radiotherapy of Prostatic Carconoma: Requirements and Experimental Results," Radiotherapy & Oncology 29, pp. 176-183 (1993).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," pp. 119-128. (1997).

Yeates, A., et al., "Simplified and Accurate CT-Guided Needle Biopsy of Central Nervous System Lesions," J. Neurosurg., vol. 37, pp. 390-393 (1982).

Zinreich, S.J., "OR Role Seen for 3-D Imaging," reprinted from Radiology Today (Feb. 1991) (2 pages).

Joskowicz et al., "Computer-Aided Image-Guided Bone Fracture Surgery: Concept and Implementation," CAR '98, pp. 710-715 (1998).

TRAJECTORY STORAGE APPARATUS AND METHOD FOR SURGICAL NAVIGATION SYSTEMS

CROSS-REFERENCE TO RELATED APPLICATIONS

This application is a continuation of U.S. patent application Ser. No. 11/128,808 filed on May 13, 2005, which is a continuation of U.S. patent application Ser. No. 10/177,739 filed on Jun. 21, 2002, now U.S. Pat. No. 6,920,347 issued on Jul. 19, 2005, which is a Continuation of U.S. patent application Ser. No. 09/545,092 filed on Apr. 7, 2000, now U.S. Pat. No. 6,535,756 issued on Mar. 18, 2003. The entire disclosures of each of the above applications are incorporated herein by reference.

BACKGROUND OF THE INVENTION

1. Field of Invention

The present invention is directed generally to image-guided medical procedures, and more particularly, to systems and methods for the storage and geometric measurement of instrument trajectories used in image-based surgical guided navigation systems.

2. Description of the Related Art

Image based surgical techniques have been used with success in aiding physicians for performing a wide variety of delicate surgical procedures. These procedures are typically used when the visualization of a surgical tool could be obscured by a patient's anatomy, or when the surgical tool is visible but the patient's anatomy may be difficult to visualize in three dimensions. Such procedures include, for example, spinal implant placement, the alignment of broken bone fragments, and the fixation of bone fractures. Prior art techniques to accurately position a surgical instrument have included the use of x-ray images to localize its position. Through the repeated acquisition of x-ray images during the procedure, real-time placement of the instrument relative to the patient's anatomy can be displayed. More recently, virtual fluoroscopically-based surgical navigation systems have been employed to track an instrument trajectory and superimpose its representation onto pre-acquired images without requiring x-rays to be repeatedly taken during the actual surgical procedure.

In many situations, a surgeon would like to create a static visual reference using the real-time and generally instantaneous instrument trajectory displayed by the surgical navigation system as the instrument progresses in the general direction of a selected, desired path. For example, some procedures require the serial placement of several implants which must be placed in a precise relative geometry. Currently, the surgeon must reacquire a new set of images after each implant is placed to properly determine the trajectory of the subsequent implant. This can be a time consuming process which increases the amount of radiation exposure to the patient and operating room personnel.

Other situations may require the surgeon to make accurate geometric measurements of a patient's anatomy. For example, some surgical procedures require the precise removal of a specific amount of bone taken in the shape of a wedge. In order to determine this amount, an angular measurement of the bone at the surgical site would assist in this procedure. Another example would be in allowing the surgeon to make distance measurement between bone implant sites to ensure proper implant placement. In light of the foregoing, there is a need for the ability to save surgical instrument trajectories and have the capability to perform measurements thereon.

SUMMARY OF THE INVENTION

The present invention is directed generally to image guided medical procedures, and, particularly, to medical procedures involving the tracking of surgical instruments. More specifically, the present invention is directed to a device and method for storing instrument trajectories.

To achieve these objects and other advantages and in accordance with the purposes of the invention, as embodied and broadly described herein, the invention is directed to an apparatus and method for the storage of trajectories and measurements which may be performed thereon for use in conjunction with image-guided surgical navigation systems.

In one aspect of the invention, an instrument trajectory is tracked in real-time by a surgical navigation system. An icon representing this real-time trajectory is overlaid on one or more pre-acquired images of the patient. At the surgeon's command, the navigation system can store the trajectory of the instrument and, if desired, create a static icon representing the saved trajectory for display on each pre-acquired image. The icon representing the stored trajectory is simultaneously displayed with the real-time trajectory's icon so the surgeon may visually compare them. The surgeon has the option of saving additional trajectories by reissuing the storage command.

In another aspect of the invention, the surgeon may measure angles between pairs of any two trajectories. The angles are computed in the plane of the image, and are, therefore, computed separately for each image displayed. One option is to compute one or more angles between the real-time trajectory and saved trajectories. These angles are preferably computed and displayed on each pre-acquired image. As the real-time trajectory changes, the displayed values are preferably updated in each image in real-time. Another option is to measure one or more angles between pairs of any two stored trajectories. As with the prior option, these angles could be computed and displayed separately for each image.

In yet another aspect of the invention, three dimensional distances between pairs of points defined by one or more sets of two trajectories can be computed and displayed. One option is to measure the distance between the real-time trajectory and one or more saved trajectories. These measurements would be computed in real-time and updated on the display as the real-time trajectory varies. Another option would be computing and displaying distances between pairs of points defined by one or more sets of two user-selected stored trajectories. For either of these two options, the defined points may be represented by the tip of each trajectory as computed by the system, or may be defined by a user-selected extension projected from the trajectory's tip.

Preferably, the invention can overcome the problems of the prior art by providing the surgeon with the visual reference and measurement information required for some surgical procedures.

Both the foregoing general description and the following detailed description are exemplary, and are intended to provide further explanation of the invention as claimed.

BRIEF DESCRIPTION OF THE DRAWINGS

The accompanying drawings, which are incorporated in and constitute a part of this specification, illustrate an embodiment of the invention and together with the description, serve to explain the principles of the invention.

DETAILED DESCRIPTION OF THE DRAWINGS

Reference will now be made in detail to the present preferred embodiments of the invention, examples of which are illustrated in the accompanying drawings. Wherever possible, the same reference numbers will be used throughout the drawings to refer to the same or like parts.

Figure 1:
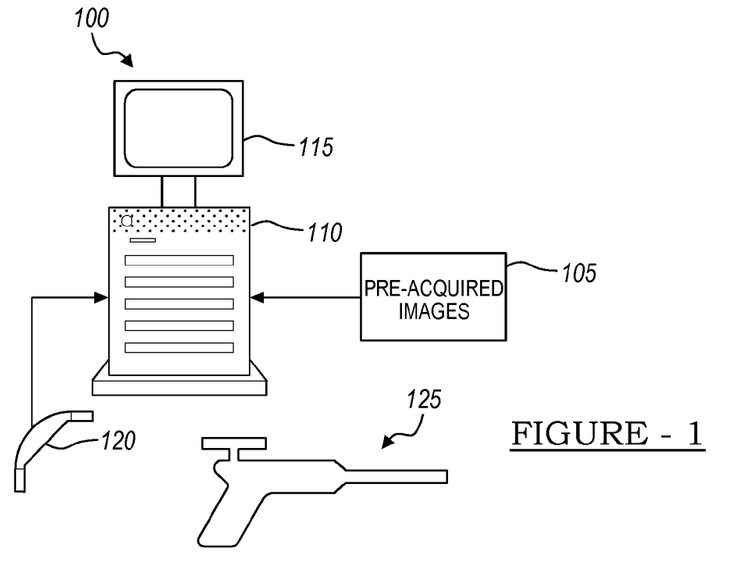
FIG. 1 is a simplified block diagram of an embodiment of a system for the storage and measurement of instrument trajectories in accordance with the present invention.

With reference to FIG. 1, there is shown schematically an apparatus in accordance with the present invention for the storage of instrument trajectories. Image-based surgical navigation system 100 enables a surgeon to generate and display on monitor 115 the trajectory of instrument 125, which is preferably a surgical instrument configured in any known manner. Data representing one or more pre-acquired images 105 is fed to navigation computer 110. Navigation computer 110 tracks the position of instrument 125 in real-time utilizing detector 120. Computer 110 then registers and displays the trajectory of instrument 125 with images 105 in real-time. An icon representing the trajectory of instrument 125 is superimposed on the pre-acquired images 105 and shown on monitor 115. At the surgeon's command, the real-time trajectory of instrument 125 can be stored in computer 110. This command also creates a new static icon representing the trajectory of the instrument on display 115 at the time the surgeon's command was issued. The surgeon has the option of issuing additional commands, each one storing an real-time trajectory and creating a new static icon for display by default. The surgeon can override this default and choose to not display any static icon. The surgeon also has the option to perform a number of geometric measurements using the real-time and stored instrument trajectories. While the present invention described in more detail below is exemplified by a fluoroscopic-based system, it is not limited to the described embodiment and could be practiced with many different types of navigation systems.

Figure 2:
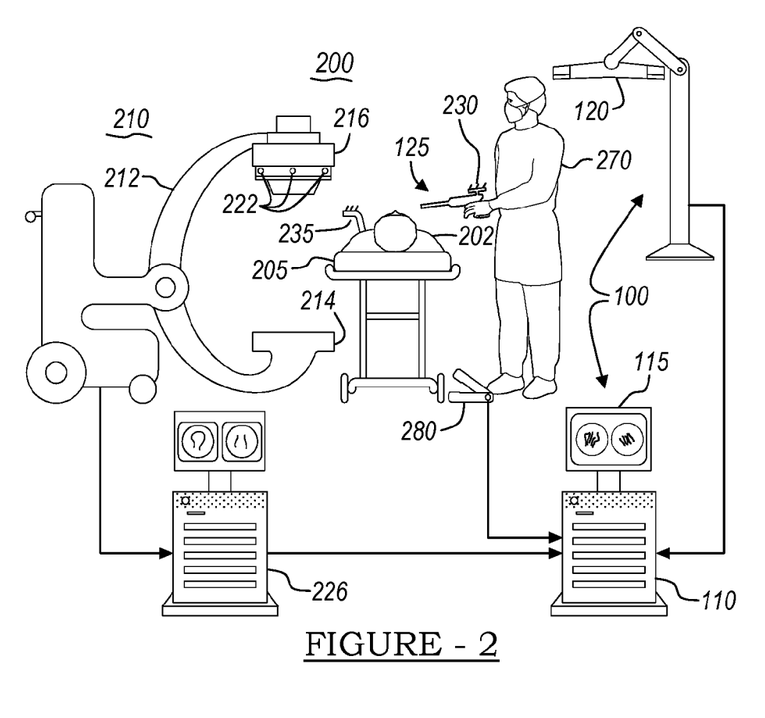
FIG. 2 is a simplified side view of an embodiment of a system for use in instrument trajectory storage and measurement in accordance with the present invention.

FIG. 2 illustrates fluoroscopic image-based surgical navigation system 200 according to the preferred embodiment of the present invention. System 200, described below in sufficient detail to allow an understanding and appreciation of the present invention, is explained in greater detail in U.S. patent application Ser. No. 09/274,972 of David A. Simon et al., entitled "Navigation Guidance via Computer Assisted Fluoroscopic Imaging," filed on Mar. 23, 1999, now U.S. Pat. No. 6,470,207 issued on Oct. 22, 2002, the entire disclosure of which is hereby incorporated by reference. However, it should be understood that the invention is not confined to use with this particular image guided surgical system.

Further referring to FIG. 2, an image-based surgical navigation system 200 for acquiring and displaying x-ray images appropriate for a given surgical procedure is shown. Pre-acquired images of patient 202 are collected when a patient, lying on platform 205, is placed within C-arm 212 of imaging device 210. The term "pre-acquired," as used herein, does not imply any specified time sequence. Preferably, however, the images are taken at some time prior to when surgical navigation is performed. Usually, images are taken from two substantially orthogonal directions, such as anterior-posterior (A-P) and lateral, of the anatomy of interest. Imaging system 210 further includes x-ray source 214 and x-ray receiving section 216 mounted on opposite sides of C-arm 212. Receiving section 216 includes target tracking markers 222. System 210 further includes C-arm control computer 226 which allows a physician to control the operation of imaging device 210. One implementation of imaging device 210 is the Model 9600 C-arm fluoroscope from OEC Medical Systems, Inc. of Salt Lake City, Utah, although tracking markers 222 are typically not included in the Model 9600 C-arm fluoroscope and may have to be added, however, the 9600 is otherwise structurally similar to imaging device 210. It is to be understood, however, that the invention is not confined to the use of this type of imaging device.

Fluoroscopic images taken by imaging system 210 are transmitted to computer 226 where they may be forwarded to surgical navigation computer 110. Computer 110 provides the ability to display the received images via monitor 115. Other devices, for example, such as heads up displays, may also be used to display the images.

Further referring to FIG. 2, image-based surgical navigation system 100 generally performs the real-time tracking of instrument 125, and, in the preferred embodiment, also tracks the position of receiver section 216 and reference frame 235. Detector 120 senses the presence of tracking markers on each object to be tracked. Detector 120 is coupled to computer 110 which is programmed with software modules that analyze the signals transmitted by detector 120 to determine the position of each object in detector space. The manner in which the detector localizes the object is known in the art, and is discussed, for example, in PCT Application No. PCT/US95/12894 (Publication No. WO 96/11624) to Bucholz, the entire disclosure of which is incorporated by reference. Any type of tracking system known in the art can be used, including, by way of example only, acoustic, optical, LED/reflectors, electro-magnetic, and/or other similar devices.

In general, instrument 125 is tracked by surgical navigation-system 100 using attached tracking markers 230 in order for its three-dimensional position to be determined in detector space. Computer 110 integrates this information with the pre-acquired images of patient 202 to produce a display which assists surgeon 270 when performing surgical procedures. An iconic representation of the trajectory of instrument 125 is simultaneously overlaid on the pre-acquired images of patient 202 and displayed on monitor 115. In this manner, surgeon 270 is able to see the trajectory of the instrument relative to the patient's anatomy in real-time.

Further referring to FIG. 2, the system according to the invention preferably has the ability to save the dynamic real-time trajectory of instrument 125. By issuing a command using foot-switch 280, for example, computer 110 receives a signal to store the real-time trajectory of the instrument in the memory of computer 110. This "storage command" also instructs computer 110 to generate a new static icon representing the saved trajectory of the instrument, essentially "freezing" the icon at the point when foot-switch 280 was closed. The static icon, along with the icon representing the real-time trajectory of the instrument, can be simultaneously superimposed over the pre-acquired image. If multiple images are being displayed, both static and real-time icons can be superimposed on all of the displayed images. Other means of issuing the storage command, such as, for example, through a graphical user interface, may also be used. The surgeon also has the option of storing multiple instrument trajectories. Each time a desired storage command is issued, the real-time trajectory of the instrument is stored in computer 110 and a new static icon representing the stored trajectory is displayed on the pre-acquired image, or if more than one image is being displayed, on all the pre-acquired images. These storage trajectory features are described in more detail below.

The system according to the invention preferably has the additional capability to measure angles between the real-time trajectory and one or more of the stored trajectories. These "dynamic angles" are measured in the image plane and are updated in real-time as the real-time trajectory varies. The computed values may then be displayed simultaneously with the pre-acquired image. If more than one pre-acquired image is being displayed, the angles for each image are preferably computed and displayed separately since they will be different for each image plane. Preferably, the system is configured to compute and display one or more angles between pairs of stored trajectories selected by surgeon 270. As with the dynamic angle measurements, the angles between the stored trajectories are computed in the image plane. They are preferably calculated and displayed separately for each displayed image. These angle calculation features will be described in more detail below.

Furthermore, the system preferably also has the ability to compute three-dimensional distances between pairs of points defined by the real-time trajectory and one or more stored trajectories selected by surgeon 270. These "dynamic distance" values are displayed with the image and vary as the instruments trajectory changes. The system also preferably has the ability to measure distances between pairs of points defined by one or more pairs of stored trajectories and to display this information with the image. For either distance measuring option, the point pairs above may be defined by the tips of the instrument trajectories, or they may be defined by extending the tips by a user-specified amount. Each of these options will be discussed in more detail below. Unlike the angle calculation, the three-dimensional distance is not a planar measurement, as such it will not vary among different images. The distance parameters may be displayed separately for each image, or, as in the preferred embodiment, may only be displayed in one location.

Image-based surgical navigation system 100 utilized in the preferred embodiment of the present invention may be the same as that used in the FluoroNav™ system, which utilizes the StealthStation® Treatment Guidance Platform, both of which are available from Medtronic Sofamor Danek, Inc.

Figure 3:
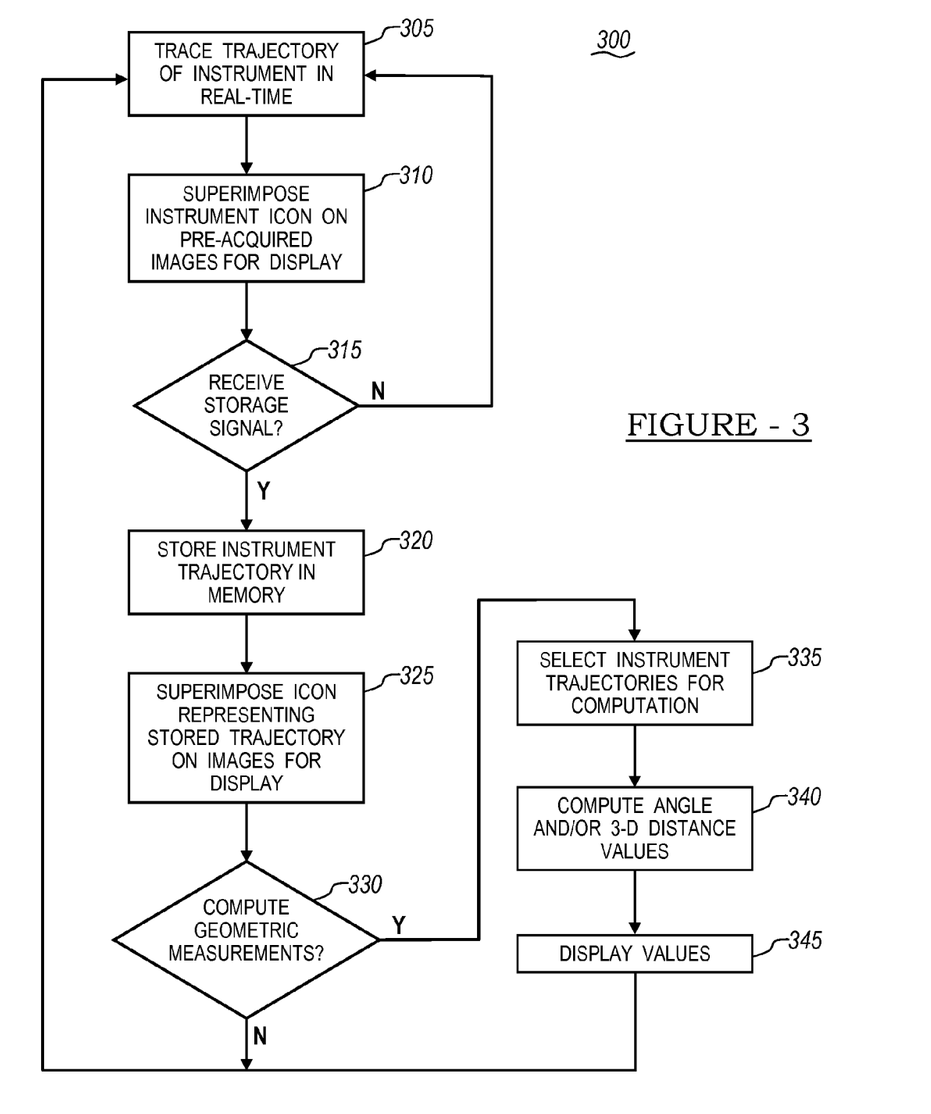
FIG. 3 is a block diagram of a process used to select, store, and compute geometric properties of trajectories in accordance with the present invention.

FIG. 3 shows flowchart 300 illustrating the preferred embodiment for storing instrument trajectories and computing geometric quantities. System 100 tracks instrument 125 by detecting tracking markers 230 with detector 120. Positions are computed in real-time in detector space by computer 110 and converted to frame space, which is a coordinate system associated with reference frame 235. The conversions used may be ones which are well known to those skilled in the art. The instrument trajectory is preferably tracked using two points, the tip and the hind, on instrument 125 which are obtained using known offsets from tracking markers 230 (step 305). The computation of the tip and hind positions is described in more detail below. An icon representing the real-time trajectory of instrument 125 may be superimposed on one or more pre-acquired images 105 (step 310). The real-time instrument tracking proceeds until the computer receives a storage command from the surgeon. In the preferred embodiment, this command is given by a signal initiated by actuation of foot-switch 280. The surgeon may also use a graphical user interface, which is described in more detail below, running on computer 110 to issue a storage command (step 315). Upon receipt of the command, computer 110 stores the real-time trajectory of instrument 125 by placing the positions of the instrument's tip and hind into memory (step 320). Computer 110 then displays an icon representing the stored trajectory which may be superimposed, along with the real-time trajectory, on the pre-acquired image. If more than one pre-acquired image is being displayed, both the stored and real-time icons can be superimposed on all pre-acquired images (step 325).

After one or more trajectories are saved, surgeon 270 has the option of computing several geometric measurements through exercising the appropriate commands on the computer's 110 graphic interface (step 330). The surgeon will then typically select which trajectories to perform the measurements upon. Measurements may be performed between the real-time trajectory and one or more user-selected stored trajectories. Alternatively, a number of measurements may also be made between pairs of user-selected stored trajectories which are chosen through the user interface (step 335). Once the trajectory pairs are chosen, surgeon 270 can select to have the angles and/or a distance measurements performed (step 340). The distance and angle calculations are described below in more detail.

Finally, the values the surgeon chose to measure can be displayed on monitor 115 simultaneously with the pre-acquired image and trajectory icons. If the measurement being performed includes the real-time trajectory, each displayed value can be updated in real-time as the position of instrument 125 changes. If multiple pre-acquired images are being displayed, the angles can be displayed on each desired image. However, in the preferred embodiment, the distance values will typically be displayed in one location. (step 345).

Figure 4:
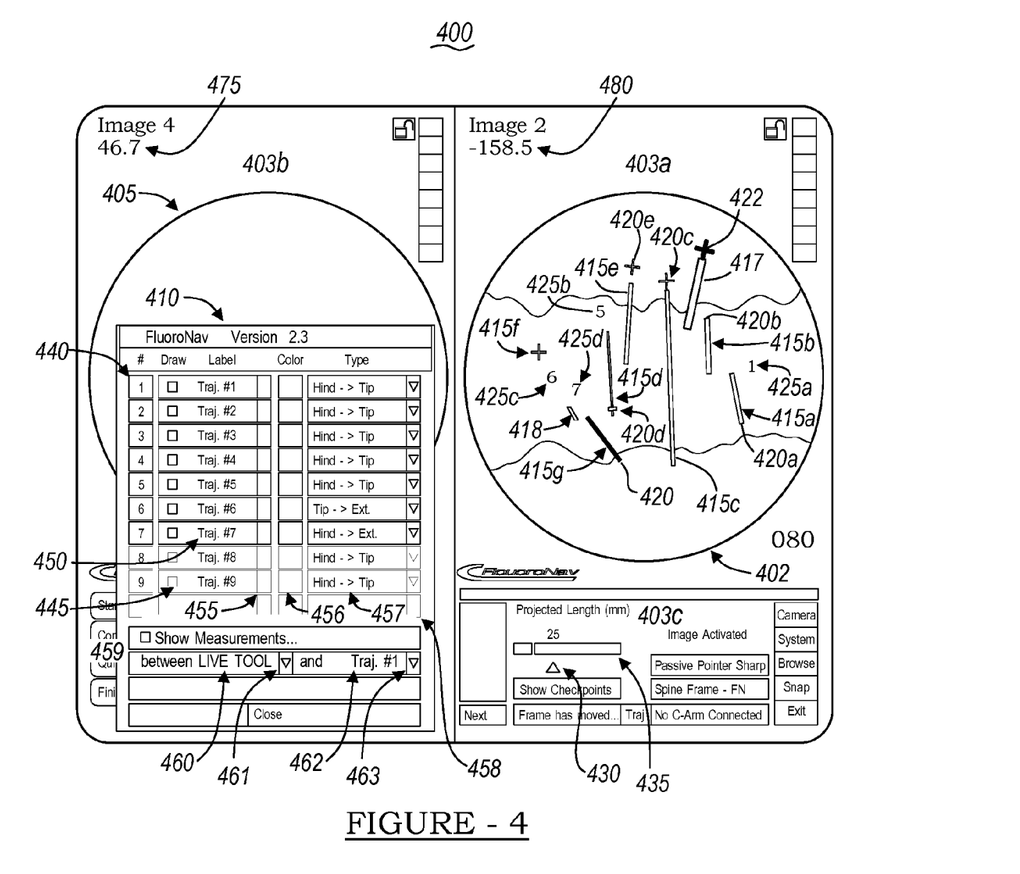
FIG. 4 is an exemplary diagram of a display in accordance with an embodiment of the invention showing several stored instrument trajectories and the real-time trajectory superimposed on two images of a patient's anatomy.

FIG. 4 shows an exemplary display which is consistent with the preferred embodiment of the invention. Display 400 preferably includes of three primary default windows, 403a-c. Two fluoroscopic images, 402 and 405, taken from different orientations of a patient, are shown in two windows, 403a-b, respectively. Control and status window 403c provides the surgeon with a set of software controls to vary the system parameters and control the modes and functionalities of the FluoroNav™ system. Note that image 405 is partially obscured by dialog box 410.

Further referring to FIG. 4, image 402 shows seven stored trajectories, 415a-g, and one real-time trajectory, 417. The hind points of each stored trajectory are denoted with cross symbols 420a-f. Note the cross symbol of trajectory 415f is not indicative of a hind point, but of an extension. Extensions will be described in more detail later. The hind point of real-time trajectory 417 is indicated by cross 422. Obviously, many other symbols other than a cross may be used to denote the hind point. Each trajectory, represented by a directional indicator such as a line, can be automatically assigned a different color and unique numerical label to easily identify it. Other types of directional indicators may also be used, and different shapes, styles, sizes, and textures can be employed to differentiate among the trajectories. Only labels 425a-d, associated with trajectories 415a, 415d, 415f, and 415g, respectively, are shown in window 403a. The surgeon has the option of not showing the label for any trajectory if desired. The surgeon also has the option of changing the default color or label text for any trajectory through the controls contained in dialog box 410. The functionality of dialog box 410 will be described in more detail below.

In certain situations, the surgeon may wish to know where the tip of the instrument would be if it were extended along a path direction indicated by its current trajectory. When software button 430 in window 403c is toggled on, computer 110 will calculate and display the icon based upon the previously set extension, as set by slider bar 435, and the current trajectory of the instrument. Toggling button 430 again will result in no extension being displayed. For example, if button 430 were previously activated and slider 435 is set to 45 mm, selecting button 430 will set the slider value to 0 mm. Activating it a second time will restore it to 45 mm. The estimated position of the tip can be calculated by computer 110 by projecting a fixed length beyond the instrument's tip in the direction of the line formed by each instrument's tip and hind. As shown in FIG. 4, an exemplary extension 418 is shown in a different line style from trajectory icon 415g. This difference could also be a change in color, type, and/or texture between extension 418 and current trajectory 415g. Computer 110 may vary the length of the extension as directed by the surgeon through manipulating control slider 435 using computer 110's mouse or keyboard. The extension feature is described in greater detail in U.S. patent application Ser. No. 09/274,972, now U.S. Pat. No. 6,470,207 issued on Oct. 22, 2002 which has been incorporated by reference. Although the look-ahead technique described above projects the graphical representation of the instrument into the image, there is no requirement that the instrument's graphical representation be in the space of the image for the extension to be projected into the image. In other words, for example, the surgeon may be holding instrument 125 above the patient and outside the space of the image, so that the representation of the instrument does not appear in the images. However, it may still be desirable to project ahead a fixed length into the image to facilitate planning of the procedure.

Further referring to FIG. 4, dialog box 410 allows the surgeon to control various aspects of how trajectories and labels are displayed. Whenever the surgeon initiates a command to store a trajectory, a row is automatically created in dialog box 410 and is identified by a number appearing in column 440. The surgeon has the option of removing a saved trajectory from display 403a by selecting the appropriate button in column 445. The color or texture of a button in column 445 can indicate the current icon display status.

Column 450 contains fields which indicate the text used in the labels for each stored trajectory. Computer 110 can select numerical values as defaults, which are illustrated in labels 425a-d, or the surgeon may select a custom label. This is accomplished by using computer 110's mouse to select the appropriate field of column 450 corresponding to the stored trajectory to be renamed. Once selected, the surgeon can use computer 110's keyboard to enter the desired text for the label. Furthermore, the label of each trajectory can be selectively displayed by activating the appropriate button in column 455 with the mouse. The color or texture of the button can be used to indicate the display status of the label for each stored trajectory. In this example, buttons corresponding to trajectories 1, 5, 6, and 7 are in the "on" state which results only in labels 425a-d being displayed in window 403a.

Selection of one of the buttons in column 456 causes the default color of the stored trajectory to be overridden by the user. Activation of the appropriate button displays a palette of colors from which one may choose to color the respective icon.

The surgeon also has the ability to select the mode of display for each icon. Selecting pull-down menu 458 allows the user to chose from one of three different display modes for each stored trajectory. The first mode, "Hind->Tip," creates an icon by drawing a line from the instruments hind position to the instruments tip position as shown in icons 415a-e. The second mode, "Tip->Ext.," creates an icon by drawing a line from the instrument's tip to the end of the extension. This mode is shown in icon 415f, which is displayed as a light colored cross to denote the extension. The third display mode, "Hind->Ext.," draws a line from the hind of the instrument to the tip of the extension. This mode is exemplified in icon 415g and extension 418. Column 457 indicates the display mode associated with each stored trajectory.

Further referring to FIG. 4, the surgeon has the option to have computer 110 compute and display measurements between selected trajectories. Button 459 commands computer 110 to display the measurements and allows the user to select which measurements to display. Pull-down menus 461, 463 allow the user to choose the trajectories which will be used to perform the measurements. Note that the real-time instrument may be used in conjunction with one or more pairs of any of the stored trajectories, or the measurements may be made against one or more pairs of any two saved trajectories. Text fields 460, 462 indicate which trajectories will be used in the measurement. The results of the measurement calculation will be displayed in windows 403a-b. In FIG. 4, the planar angle between real-time trajectory 417 and stored trajectory 415a is shown at 470 in window 403b and 480 in window 403a. The difference between values 470 and 480 is due to the different planar geometries associated with images 402 and 405.

Figure 5:
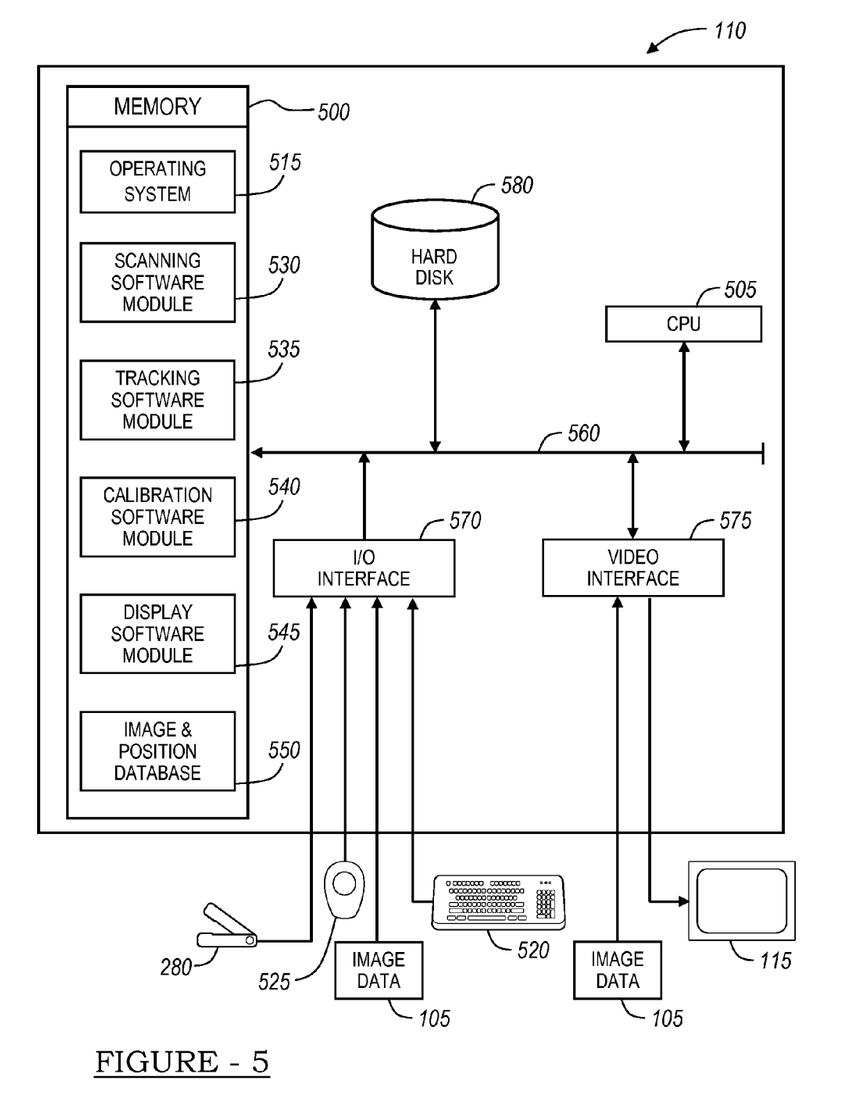
FIG. 5 is a simplified block diagram of an exemplary computer system used in the surgical navigation system in accordance with one embodiment of the invention.

Referring to FIG. 5, components and modules of a computer system 110 used to perform various processes of the present invention are described. Although a STEALTH STATION® image guided system manufactured by Medtronic Sofamor Danek has been identified, it will be appreciated that the present invention may be utilized with other types of computer systems. One aspect of the computer system 110 includes a graphical user interface system operating in conjunction with a display screen of a display monitor 115. The graphical user interface system is preferably implemented in conjunction with operating system 515 running computer 110 for displaying arid managing the display objects of the system. The graphical user interface is implemented as part of the computer system 110 to receive input data and commands from a conventional keyboard 520 and mouse 525. Footswitch 280 is also configured to enable the user to initiate the storage of instrument 125's real-time trajectory. For simplicity of the drawings and explanation, many components of a conventional computer system have not been illustrated such as address buffers, memory buffers, and other standard control circuits because these elements are well known in the art and a detailed description thereof is not necessary for understanding the present invention.

A computer program used to implement the various steps of the present invention is generally located in memory unit 500, and the processes of the present invention are carried out through the use of a central processing unit (CPU) 505. Those skilled in the art will appreciate that the memory unit 500 is representative of both read-only memory and random access memory. The memory unit also contains a database 550 that stores data, for example, image data and tables, including such information as stored instrument tip and hind positions, extension values, and geometric transform parameters, used in conjunction with the present invention. CPU 505, in combination with the computer software comprising operating system 515, scanning software module 530, tracking software module 535, calibration software module 540, and display software module 545, controls the operations and processes of computer system 110. The processes implemented by CPU 505 may be communicated as electrical signals along bus 560 to an I/O interface 570 and a video interface 575.

Scanning software module 530 performs the processes associated with creating a coordinate reference system and reference images for use in connection with the present invention and are known to those skilled in the art. Tracking software module 535 performs the processes necessary for tracking objects in an image guided system as described herein and are known to those skilled in the art. Calibration software module 640 computes the geometric transform which corrects for image distortions and registers the images to the anatomical reference frame 235, and thus the patient's anatomy.

Display software module 545 applies, and if desired, computes the offsets between the guide tracking markers 230 and the tip and hind of the instrument in order generate an icon representing the trajectory of the instrument for superposition over the images. For instruments with fixed lengths and angulations, these offsets can be measured once and stored in database 550. The user would then select from a list of instruments, the one being used in the procedure so the proper offsets are applied by display software module 545. For instruments with variable lengths and angulations, the offsets could be measured manually and entered via keyboard 520, or measured using the navigation system 100 in conjunction a tracked pointer or tracked registration jig (not shown). If a tracked pointer is used, the user will touch the tip and tail of the instrument while it is being tracked. The offsets are computed by display software module 545 and stored for later use. Similarly, if a tracked registration jig is used, the instrument is placed within the jig while it is being tracked. The jig will measure the extremities of the instrument and display software module 545 will again compute the offsets and store them for later use in database 550.

Pre-acquired image data 105 can be fed directly into computer 110 digitally through I/O interface 570, or may be supplied as video data through video interface 575. In addition, items shown as stored in memory can also be stored, at least partially, on hard disk 580 if memory resources are limited. Furthermore, while not explicitly shown, image data may also be supplied over a network, through a mass storage device such as a hard drive, optical disks, tape drives, or any other type of data transfer and storage devices which are known in the art.

Figure 6:
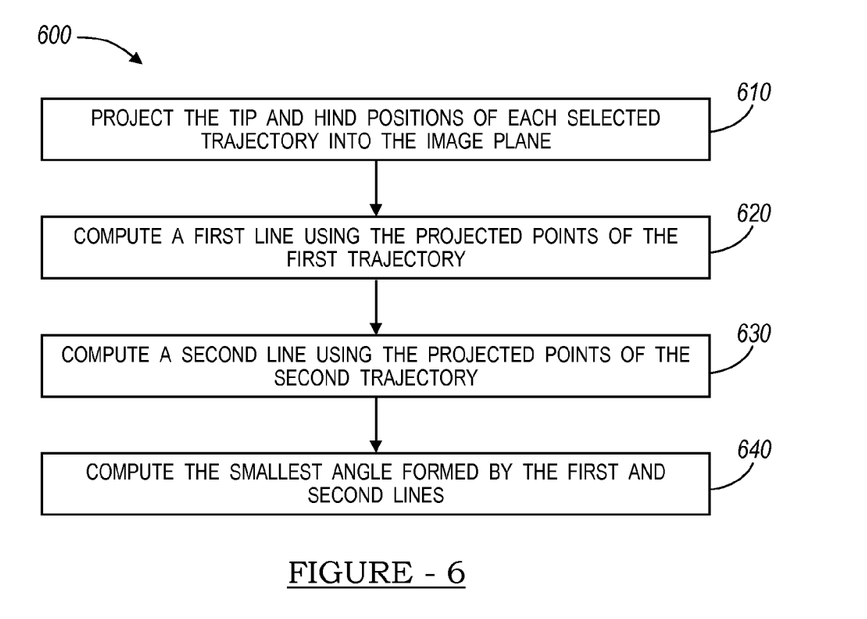
FIG. 6 is a block diagram of a process used compute the angle between two trajectories in accordance with the present invention.

FIG. 6 shows a block diagram illustrating a method for calculating a planar angle between two trajectories for the preferred embodiment. After surgeon 270 selects the trajectories using pull-down menus 461,463 as described above, the tip and the hind positions of each trajectory are projected into the image plane. Since x-ray receiving section 216 is tracked by navigation system 100 utilizing tracking markers 222, the coordinates of the image plane are well defined. Using the tip, hind, and image plane coordinates, the projection is performed using techniques well known to those skilled in the art (610). A first line segment is constructed by connecting the projected tip and hind points corresponding to the first trajectory computed above (step 620). In the same manner, a second line segment is constructed utilizing the projected points of the second trajectory (step 630). The angle corresponding to the intersections of the two aforementioned line segments can then be computed by techniques known to those skilled in the art (step 640).

Figure 7:
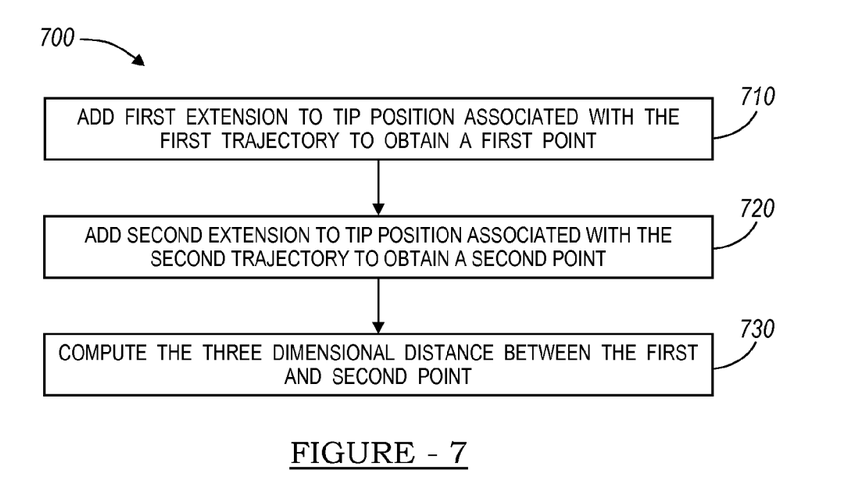
FIG. 7 is a is a block diagram of a process used compute the distance between the tips of two trajectories in accordance with the present invention.

FIG. 7 shows a block diagram illustrating a method of the preferred embodiment for calculating a distance between points in space as defined by two trajectories. After surgeon 270 selects two trajectories using pull-down menus 461, 463 in the manner described above, a first point is determined using the three-dimensional tip position of the first trajectory as computed by navigation system 100. If a "look-ahead" extension is associated with the first trajectory, it is added to the tip position (step 710). A second point associated with the second trajectory is computed in the same manner as described for step 710 (step 720). The distance may then be computed using the three-dimensional coordinates of the first and second points by a standard Euclidean distance formula which is well known in the art.

The foregoing description is presented for purposes of illustration and explanation. It is not intended to be exhaustive or to limit the invention to the precise form disclosed, and modifications of variations are possible in light of the above teachings or may be acquired from practice of the invention. The principles of the invention and its practical application enable one skilled in the art to utilize the invention in various embodiments and with various modifications as are suited to the particular use contemplated.

For example, pre-acquired images obtained from different modalities may be used in place of those produced by the C-arm fluoroscope x-ray imager. Such modalities include, by way of example only, computer tomography, ultrasound, PET, or magnetic resonance imaging.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of determining a trajectory of an object during a procedure, comprising:
    tracking a three-dimensional position of the object with a tracking system;
    storing a first location of the object based on a first tracked location of the object with the tracking system;
    executing instructions with a computer processor to determine a second location of the object based on a second tracked location of the object with the tracking system;
    generating a first representation of the object at the first location;
    generating a second representation of the object at the second location; and
    displaying on a display simultaneously both the first representation of the object at the first location and the second representation of the object at the second location.

2. The method of claim 1, further comprising:
    displaying image data of a patient on the display;
    wherein displaying both the first representation and the second representation on the display includes superimposing the both first representation and the second representation on the displayed image data.

3. The method of claim 1, further comprising:
determining at least one of an angle between the first representation and the second representation and a three-dimensional distance between an end of the first representation and an end of the second representation.

4. The method of claim 3, further comprising:
displaying with the display at least one of the determined angle between the first representation and the second representation or the three-dimensional distance between the end of the first representation and the end of the second representation.

5. The method of claim 3, further comprising:
displaying a dynamic determined three-dimensional distance between the end of the first representation and the end of the second representation as the object is tracked relative to the first location.

6. The method of claim 3, wherein storing the first location of the object tracked with the tracking system is due to a signal received by the computer processor.

7. The method of claim 6, further comprising:
executing instructions with the computer processor to freeze the first representation based on the tracked first location of the object.

8. The method of claim 1, further comprising:
determining, by executing instructions with the computer processor, a distance from an end the first representation and an end of the second representation; and
determining, by executing instructions with the computer processor, a distance between the end of the first representation and the end of the second representation.

9. The method of claim 1, wherein the second location of the object is a current location of the object and the stored location of the object is a previous location of the object that is different from the current location of the object.

10. A method of determining a trajectory of an object during a procedure, comprising:
tracking a three-dimensional position of the object with a tracking system at a first time and at a second time later than the first time;
executing instructions with a computer processor to determine a first location of the object tracked with the tracking system at the first time;
storing the first location of the object;
executing instructions with the computer processor to determine a second location of the object tracked with the tracking system at the second time, wherein the first location is different than the second location;
generating a first representation of the object at the first location;
generating a second representation of the object at the second location; and
displaying on a display simultaneously both the generated first representation of the object and the generated second representation of the object.

11. The method of claim 10, further comprising:
displaying an image of the object with the display, including both the generated first representation of the object and the generated second representation of the object simultaneously superimposed on the displayed image of the subject.

12. The method of claim 11, wherein executing instructions with the computer processor to determine the first location is determining a previous location and the second location is a current location of the object.

13. The method of claim 12, wherein executing instructions with the computer processor to determine the first location is substantially freezing a representation of the current location of the object at the first time for display on the display upon receipt of a signal to save the first location relative to a second location of the object, wherein the second location is a current location of the object at the second time.

14. The method of claim 12, further comprising:
receiving a signal to generate a static representation of the first location of the object;
wherein storing the first location and generating the first representation of the object at the first location is based on the received signal.

15. The method of claim 14, wherein receiving the signal to generate the first representation includes receiving a plurality of signals to generate a first plurality of distinct first representations.

16. The method of claim 15, further comprising:
computing with the computer processor a distance between at least one distinct representation of the first plurality of distinct first representations and the second location of the object.

17. The method of claim 16, further comprising:
displaying the computed distance; and
varying the computed distance based upon the tracked second location of the object.

18. The method of claim 14, wherein the first location includes a first plurality of locations, and further including computing with the computer processor a distance between at least one first location of the first plurality of locations and the second location of the object.

19. The method of claim 18, further comprising:
displaying the computed distance.

20. A method of determining a trajectory of an object during a procedure, comprising:
tracking a three-dimensional position of the object with a tracking system at a first time and at a second time later than the first time;
receiving a signal by a computer processor to store a first location of the object tracked with the tracking system at the first time;
storing, based on the received signal, the first location of the object;
determining a second location of the object tracked with the tracking system at the second time later than the first time by executing instructions with the computer processor; and
displaying on a display simultaneously both a generated first representation of the object and a generated second representation of the object;
wherein the displayed first representation and the second representation are generated by the computer processor based on the tracked first location and the tracked second location.

21. The method of claim 20, wherein determining the second location is determining a current location of the object tracked by the tracking system.

22. The method of claim 21, further comprising:
displaying an image of the object with the display;
wherein displaying on the display both the generated first representation of the object and the generated second representation of the object includes superimposing simultaneously both the generated first representation and the generated second representation on the displayed image of the subject.

23. The method of claim 22, further comprising:
computing with the computer processor a distance between the stored first location of the object and the determined second location of the object; and
displaying the computed distance.

24. The method of claim 23, further comprising:
varying the computed distance based upon the determined second location of the object;
wherein the object varies in three-dimensional distance relative to the stored first location due to moving the object.

25. The method of claim 22, further comprising:
computing with the computer processor an angle between the stored first location of the object and the determined second location of the object; and
displaying the computed angle.

26. The method of claim 25, further comprising:
varying the computed angle based upon the determined second location of the object;
wherein the object varies in three-dimensional angle relative to the stored first location due to moving the object.

* * * * *